US00PP22799P3

(12) United States Plant Patent
Ferare

(10) Patent No.: US PP22,799 P3
(45) Date of Patent: Jun. 19, 2012

(54) DAYLILY PLANT NAMED 'DOUBLE PARDON ME'

(50) Latin Name: *Hemerocallis hybrida*
Varietal Denomination: Double Pardon Me

(75) Inventor: Jacques Ferare, Hollister, CA (US)

(73) Assignee: CP Delaware, Inc., Wilmington, DE (US)

( * ) Notice: Subject to any disclaimer, the term of this patent is extended or adjusted under 35 U.S.C. 154(b) by 79 days.

(21) Appl. No.: 12/805,091

(22) Filed: Jul. 12, 2010

(65) Prior Publication Data

US 2012/0011628 P1 Jan. 12, 2012

(51) Int. Cl.
*A01H 5/00* (2006.01)

(52) U.S. Cl. ..... Plt./312

(58) Field of Classification Search ..... Plt./312
See application file for complete search history.

*Primary Examiner* — Howard Locker
(74) *Attorney, Agent, or Firm* — Buchanan Ingersoll & Rooney PC

(57) ABSTRACT

A new and distinct *Hemerocallis* cultivar of the dormant type is provided. The new cultivar is very floriferous and forms attractive ruffled double red flowers displaying substantial substance, and a funnel-shaped form over an extended period of time. In U.S.D.A. Hardiness Zone No. 6b, blooming commonly begins during mid- to late-June and commonly ends during early- to mid-September. The new cultivar displays a plurality of fans and a plurality of scapes per fan. The flowers well withstand rain in view of the strength of the tepals. The new cultivar readily can be distinguished from the 'Pardon Me' cultivar (non-patented in the United States) in view of the consistent display of a substantially greater number of tepals per blossom. The new cultivar is particularly well suited for growing as distinctive colorful ornamentation in the landscape.

1 Drawing Sheet

Botanical/commercial classification: *Hemerocallis hybrida*/Daylily.

Varietal denomination: cv. Double Pardon Me.

SUMMARY OF THE INVENTION

The present invention comprises a new and distinct cultivar of *Hemerocallis* plant of the dormant type, and hereinafter is referred to by the cultivar name 'Double Pardon Me'.

The new cultivar of the present invention originated in a production block among 'Pardon Me' *Hemerocallis* plants growing near West Grove, Pa., U.S.A. The 'Pardon Me' plants growing in the block had been asexually reproduced by division. A single plant of the new cultivar was removed and isolated from the block and was thereafter preserved and studied in order to determine its possible characterization as being a new and distinct cultivar. It has been concluded as a result of this study that the new cultivar of the present invention is a spontaneous whole plant mutation of the 'Pardon Me' cultivar of unknown causation. It further has been determined that the new cultivar can be consistently distinguished from the 'Pardon Me' cultivar through the display of a dissimilar highly attractive inflorescence. More specifically, the new cultivar upon study and observation was found to reliably form a significantly greater number of tepals per blossom than the 'Pardon Me' cultivar. It was determined that the new 'Double Pardon Me' cultivar consistently forms eighteen (18) tepals per blossom, while the parent 'Pardon Me' cultivar displays exclusively single blossoms having only six (6) tepals. This finding with respect to the characterization of the new cultivar has been additionally observed during a number of subsequent growing seasons prior to the release of the new cultivar to the public.

It was found that the new *Hemerocallis* plant of the present invention is of the dormant type and:

(a) forms attractive ruffled double red funnel-shaped flowers having substantial substance,
(b) possesses a long blooming season with substantial repeat blooming,
(c) exhibits a propensity to readily display a plurality of fans, and
(d) readily forms a plurality of scapes per fan over the flowering season.

In U.S.D.A. Hardiness Zone No 6b blooming commonly begins during mid- to late-June and commonly ends during early- to mid-September. The blossoms well withstand rain in view of the strength of the tepals.

As indicated, the 'Double Pardon Me' plant exhibits attractive ruffled funnel-shaped red flowers that readily can be distinguished from the parent 'Pardon Me' by the double nature of the blossoms. In all instances the blossoms of the 'Pardon Me' cultivar are single.

Asexual reproduction of the new cultivar by division has been carried out near West Grove, Pa., U.S.A. More specifically, a clump of the new cultivar was removed from the field and the fans were divided. It has been demonstrated that the characteristics of the new cultivar are firmly fixed and are well retained following this asexual reproduction.

The 'Double Pardon Me' plant has not been observed under all possible environmental conditions to date. Accordingly, it is possible that the phenotype may vary somewhat with variations in the environment, such as temperature, light, day length, contact with pesticides, etc.

BRIEF DESCRIPTION OF THE PHOTOGRAPH

The accompanying photograph was prepared during July 2004 and shows as nearly true as it is reasonably possible to make the same in color illustrations of this character, typical foliage, floral buds in various stages of development, and fully open blossoms of the new cultivar of the present invention.

The illustrated plants were being grown outdoors in containers near West Grove, Pa., U.S.A. The double nature of the attractive red blossoms is apparent. The fully opened blossoms depicted in the photograph had undergone some fading.

DETAILED DESCRIPTION

The chart used in the identification of the colors described herein is The R.H.S. Colour Chart of The Royal Horticultural Society, London, England. In some instances, more common color terms are provided and are to be accorded their usual dictionary significance. A one-year-old plant is described while growing outdoors in a container during June near West Grove, Pa., U.S.A.

Plant:

*Height*.—Approximately 33 cm at an age of one year.

*Width*.—Approximately 50 cm at an age of one year.

*Foliage*.—Form: single stem, substantially erect fan-shaped base having narrow arching, long, keeled, grass-like glabrous slightly textured leaves that are two-ranked at the base of the scape. Quantity: abundant, with a mature plant commonly having approximately 18 leaves per fan. Leaf Size: commonly approximately 1.5 cm in width on average, and approximately 30 cm in length on average. Leaf Shape: linear and long-keeled with entire margins. Texture: glabrous. Color: Yellow-Green Group 146A. Type: dormant with the leaves commonly retaining little or no green coloration during the winter in U.S.D.A. Hardiness Zone No. 6b.

*Scape*.—Color: Yellow-Green Group 146B. Length: commonly approximately 25 cm on average.

*Disease tolerance*.—Generally comparable to that of 'Pardon Me' cultivar. When conditions of stress are encountered (e.g. absence of water) during the hot humid days of summer, some leaf streaking has been observed.

Inflorescence:

*Bud*.—Form: modified oblanceolate. Size: on the day prior to opening commonly approximately 5 cm in length on average, and approximately 1.5 cm in width on average. Opening Rate: commonly approximately three hours on average. Peduncle Character: rigid and sturdy. Peduncle Color: Yellow-Green Group 144B.

*Flower*.—Size: commonly have a diameter of approximately 9 cm on average and a depth of approximately 5 cm on average. Borne: singly on the branchlets of a sturdy erect rachis. Blooms Per Scape: commonly approximately 1 or 2 each day. Tepalage: each flower consists of eighteen (18) tepals regularly arranged around the perianth. This can be compared to six (6) tepals for the 'Pardon Me' cultivar. Outer Tepal Shape: oblanceolate with slightly ruffled or undulated entire margins and an acuminate apex. Outer Tepal Texture: slightly ribbed. Outer Tepal Size: commonly approximately 5.5 cm in length on average and approximately 2.5 cm in width on average. Outer Tepal Color: upon opening generally Greyed-Purple Group 185A with Yellow-Green Group 151A at the base. Inner Tepal Texture: ruffled edge. Inner Tepal Size: commonly approximately 5 cm in length on average and approximately 1.5 cm in width on average. Inner Tepal Color: upon opening generally Greyed-Purple Group 185A with Yellow-Green Group 151B at the base. Blooming Habit: the flowers commonly bloom substantially continuously and the scape commonly is substantially continuously in bloom for up to approximately 90 days per year in Hardiness Zone No. 6b. Effects of Weather: the flowers commonly well withstand rain damage in view of the strength of the tepals. Lasting Quality: commonly at least 16 hours. As with other *Hemerocallis* cultivars, the flower color eventually fades somewhat during the day with the natural effects of environmental conditions and ongoing maturity. Upon fading the inner tepals commonly assume a coloration of near Red-Purple Group 63A. Fragrance: none.

*Reproductive organs*.—None encountered during observations to date, and accordingly the plant appears to be sterile during observations to date.

*Fruit*.—None encountered during observations to date.

Hardiness: The plant has been observed to be very tolerant to cold. It displays hardiness in U.S.D.A. Hardiness Zone No. 5 where temperatures as low as −20° F. have been encountered.

Heat tolerance: The plant also has been observed to be very tolerant to heat, and has withstood temperatures as high as 100° F.

I claim:

1. A new and distinct cultivar of *Hemerocallis* plant of the dormant type, substantially as herein shown and described, which:

(a) forms attractive ruffled double red funnel-shaped flowers having substantial substance, (b) possesses a long blooming season with substantial repeat blooming, (c) exhibits a propensity to readily display a plurality of fans, and (d) readily forms a plurality of scapes per fan over the flowering season;

substantially as illustrated and described.

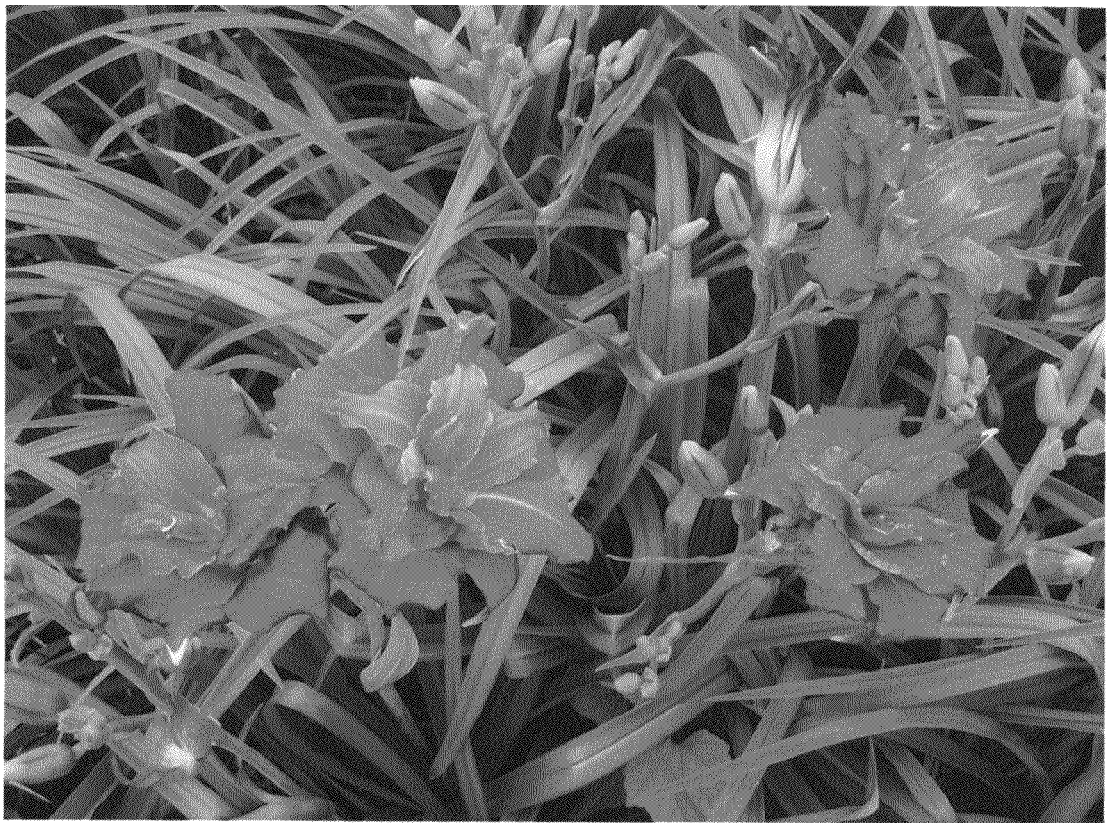

* * * * *